United States Patent [19]

Powell

[11] 3,993,648

[45] Nov. 23, 1976

[54] TETRAHYDRO-2-(NITROMETHYLENE)-2H-1,3-THIAZINES

[75] Inventor: James E. Powell, Rodmersham Green near Sittingbourne, England

[73] Assignee: Shell Oil Company, Houston, Tex.

[22] Filed: Mar. 29, 1976

[21] Appl. No.: 671,227

Related U.S. Application Data

[63] Continuation-in-part of Ser. No. 554,361, March 3, 1975, abandoned, which is a continuation-in-part of Ser. No. 468,124, May 8, 1974, abandoned.

[52] U.S. Cl. .............................. 260/243 R; 424/246

[51] Int. Cl.² ...................................... C07D 219/06
[58] Field of Search ................................ 260/243 R

[56] References Cited

UNITED STATES PATENTS 3,962,233    6/1976    Roman ................................ 260/243

*Primary Examiner*—John M. Ford

[57] ABSTRACT

Novel insecticidal tetrahydro-2-(nitromethylene)-2H-1,3-thiazines.

7 Claims, No Drawings

TETRAHYDRO-2-(NITROMETHYLENE)-2H-1,3-THIAZINES

This application is a continuation-in-part of application Ser. No. 554,361, filed Mar. 3,1975, now abandoned, which is a continuation-in-part of application Ser. No. 468,124, filed May 8, 1974, now abandoned.

DESCRIPTION OF THE INVENTION

It has been found that useful insecticidal activity is possessed by certain tetrahydro-2-(nitromethylene)-2H-1,3-thiazines. These compounds have been found to be resonance hybrids, the principal forms contributing thereto being described by the formulae:

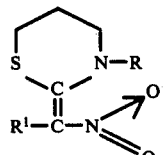 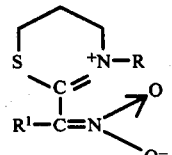

(A)         (B)

wherein the symbols have the respective meanings set out hereinafter. When the symbol, R, represents a hydrogen atom, the resonance hybrid als may exist in two tautomeric forms, one form being the resonance hybrid described above and the other being represented by the formula

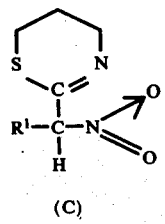

(C)

This form, C, can be designated as a 2-($R^1$-nitromethyl)-5,6-dihydro-4H-1,3-thiazine. The left-hand form of the resonance hybrid (i.e., form A) can be designated as a 3-R-tetrahydro-2-(nitromethylene)-2H-1,3-thiazine, while the right-hand form of the hybrid (i.e., form B) can be designated as a 3-R-2-(aci-nitromethyl)-5,6-dihydro-4H-1,3-thiazinium hydroxide inner salt.

The resonance hybrid may exist as either of two geometric (cis-trans) isomers, depending upon the spatial relationship of the moieties about the bond between the carbon atom of the nitromethylene moiety and the ring carbon atom to which it is joined.

In this specification, for the sake of simplicity, these compounds will be referred to generally as tetrahydro-2-(nitromethylene)-2H-1,3-thiazines. This terminology is intended to include all of the contributors to the resonance hybrid, the geometric isomers, and the tautomers, as well as mixtures thereof.

In these compounds, the symbols used in the formulae having the following meanings, respectively:

R is hydrogen, alkyl, alkenyl, alkoxyalkyl, cycloalkylalkyl, cyanoalkyl, haloalkenyl, aralkyl or alkoxycarbonylvinyl.

$R^1$ is hydrogen or alkyl, alkenyl, alkynyl, haloalkyl, haloalkenyl, halo(hydroxy)alkyl, alkoxyalkyl, cyanoalkyl, hydroxyalkyl, alkoxycarbonylalkyl, alkylcarbonylalkyl, alkylthioalkyl, alkylsulfinylalkyl, aryl, aralkyl or arylthio optionally substituted on the ring by one or more of halogen, nitro, cyano, alkyl, aryl, alkoxy or aryloxy; halogen; aminomethyl, $-CH_2-NR^2R^3$, $R^2$ is alkyl, hydroxyalkyl, alkoxyalkyl, cycloalkyl, alkenyl, aryl, haloaryl, or aralkyl, and $R^3$ is hydrogen or one of the moieties represented by $R^2$;

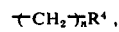

wherein n is zero, one or two, and $R^4$ is a heteromonocyclic moiety of from five to six carbon atoms in the ring, containing in the ring carbon atoms and one to two of oxygen (—O—), sulfur (—S—) and nitrogen (=N- or -NH-) bonded to carbon in the ring; or is

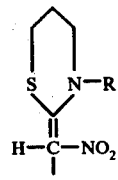

In all cases, each alkyl, cycloalkyl, alkenyl, alkynyl or alkylene moiety suitably contains no more than eight and preferably no more than four carbon atoms and each may be of straight-chain or branched-chain configuration.

The preferred aryl moieties are optionally substituted phenyl. The preferred aminoalkyl moieties are dialkylaminomethyl. The preferred aralkyl moieties are optionally-substituted phenylmethyl. Preferred heterocyclic ($R^4$) moieties are furanyl, tetrahydrofuranyl, dioxolanyl, thienyl, thiopyranyl, pyridinyl, pyrrolidinyl and morpholinyl, and their $R^4$-methyl- counterparts.

Also, when R is hydrogen, the invention includes salts of that subclass of compounds— i.e., R is a cationic species. The contemplated salts are alkali metal salts, alkyl halide salts, ammonium salts and amine salts generally, and particularly salts of alkyl- and alkanolamines, and polyamines. Included are the salts of mono-, di- and tri-alkyl, alkanol, alkenyl and mono- and poly-(alkoxy)alkylamines, and polyamines in which each alkyl, alkenyl, alkanol, or alkoxyalkyl moiety contains from one to twenty carbon atoms or more including, but not necessarily limited to, one or more of dimethylamine, diethanolamine, trimethylamine, oleyl propylenediamine, n-dodecylamine, n-tetradecylamine, n-hexadecylamine, n-octadecylamine, heptylamine, triethanolamine, tert-$C_{11-14}$ and tert-$C_{18-24}$ primary amines, oleylamine, coco amine, hydrogenated tallow amine, tallow amine, soya amine, dicoco amine and di(hydrogenated tallow) amines, dimethyl hexadecylamine, dimethyl octadecylamine, dimethyl coco amine, dimethyl soya amine, N-coco propylenediamine, N-soya propylenediamine, N-tallow propylenediamine, and the like.

Of particular interest because of the activity of the members thereof is the sub-class of this genus of compounds wherein R is hydrogen.

For illustration, preparation of typical species of the genus is described in the examples included hereinafter. Other typical, illustrative species of this genus of tetrahydro-2-(nitromethylene)-2H-1,3-thiazines include those wherein the symbols represent the following moieties, this manner of naming these species being accurate, yet pointing out the differences between the different species more clearly than if the entire, complicated name of each species were to be given:

$R^1$ = H, R =
2-propenyl
3-chloro-2-propenyl
2-cyanoethyl
methoxymethyl
2-(cyclohexyl)ethyl
cyclopropylmethyl R = H, $R^1$ =
methyl
2-hydroxyethyl
methoxymethyl
(methylthio)methyl
methoxycarbonylmethyl
2-propynyl
3-chloro-2-propenyl
(dipropylamino)methyl
(bis(2-hydroxyethyl)amino)methyl
(bis(2-methoxyethyl)amino)methyl
dicyclohexylaminomethyl
(diphenylamino)methyl $R^1$ = (dimethylamino)methyl, R =
methyl
2-chloro-2-propenyl $R^1$ = 2-propenyl, R =
methyl Compounds of this invention can be prepared by several general procedures:

Method A: treating a nitroketene dimethyl mercaptole (NKDM) (R. Gompper & H. Schaefer, Berichte, 100, 591 (1967)) with a 3-amino-1-propanethiol (S. D. Turk, et al., J. Org. Chem., 27, 2846 (1962)), including suitably substituted 3-amino-1-propanethiols, referring to the definitions of R and $R^2$.

Method B: treating 5,6-dihydro-2-(methylthio)-4H-1,3-thiazine (A. F. McKay et al., J. Am. Chem. Soc., 80, 3339 (1958)) with an alkyl nitroacetate (S. Zen, et al., Kogyo Kagaku Zasshi, 74, 70 (1971)) in the presence of a catalytic amount of zinc ion (e.g., zinc chloride) to form the alkyl nitro(tetrahydro-2H-1,3-thiazine-2-ylidene)acetate, which is hydrolyzed with a base and decarboxylated by acidification to give the desired product.

Method C: substituting a moiety, R, on the ring nitrogen atom by treating tetrahydro-2-(nitromethylene)-2H-1,3-thiazine, which can be prepared by either of Methods A or B with a strong alkali metal base in a liquid mixture of tetrahydrofuran and hexamethylphosphoramide, or with an alkali metal derivative of the appropriate alcohol in an alcohol as solvent, then treating the resulting intermediate with the appropriate R-sulfate, iodide, chloride, bromide or tosylate.

Method D: involves a Michael Reaction wherein the nitromethylene thiazine is treated with a compound containing an activated olefinic double bond which will react at the alpha carbon atom of the thiazine. This method is illustrated in Examples 9, 11 and 12 hereinafter.

Method E: compounds of this invention wherein $R^1$ is halogen can be prepared by direct halogenation, by elemental halogen or by a halogenated compound containing positive halogen, of the appropriate R = H precursor.

Method F: 5,6-dihydro-2-(methylthio)-4H-1,3-thiazine is treated with an appropriate alkylating agent in an aprotic high dielectric constant solvent, and the product is treated with nitromethylpotassium in a protic high dielectric constant solvent.

Method G: tetrahydro-2-(nitromethylene)-2H-1,3-thiazine is heated with a suitably reactive alkylating agent, without or with a suitable solvent.

Method H: tetrahydro-2-(nitromethylene)-2H-1,3-thiazine is treated with a reactive aldehyde in a suitable solvent, the product being isolated and purified by conventional techniques.

Method I: involves a Mannich Reaction, wherein tetrahydro-2-(nitromethylene)-2H-1,3-thiazine is treated with a secondary amine or with a dihaloaniline with the resulting mixture being treated with formaldehyde to form the substituted aminomethyl nitromethylenethiazine.

Method J: Compounds of the invention wherein $R^1$ is $-CH_2-NR^2R^3$ can be prepared by treating 2-nitro-2-(tetrahydro-2H-1,3-thiazin-2-ylidene)ethanol ($R^1$ = $-CH_2OH$) with the appropriate amine, $H-NR^2R^3$.

Method A is carried out by mixing the reactants in a suitable liquid medium such as a lower alkanol. The reaction can in some cases be carried out at essentially room temperature while in other cases gentle to moderate heating (up to 100° C) may be required. Generally, it will be found best to employ a slight to moderate excess (5–25%) of the thiol over that theoretically required to react with the mercaptole. For best resuls, oxygen should be excluded from the reaction zone by conducting the reaction in a nitrogen atmosphere. The product can be recovered by removing the solvent, digesting the residue with water and then extracting the desired product from the aqueous phase by means of a suitable solvent such as methylene chloride.

Method B can be conducted by gradually treating the thiazine with a slight to moderate (5–20%) excess of the alkyl nitroacetate at a moderately elevated temperature, e.g. 80°–130° C, in the presence of a catalytic amount of zinc ion which conveniently is supplied as zinc chloride, to form the thiazine acetate intermediate. While a suitable solvent may be used, in some cases at least, one will not be required. The product can be worked up by conventional extraction and crystallization techniques. The acetate then is decarboxylated by treatment (hydrolysis) with excess base, followed by neutralization of the mixture and recovery of the product. The hydrolysis can be effected at room temperature or at slight to moderately elevated temperatures. Product work-up again can be effected by conventional filtration, extraction, crystallization and elution (chromatographic) techniques.

In method C the thiazine is substituted on the ring nitrogen atom by treating the thiazine with about an equimolar amount of a strong alkali metal base in a suitable liquid reaction medium at room temperature or at a slight to moderately elevated temperature, then treating the resulting mixture with about the theoretical amount of the sulfate, iodide, bromide, chloride or tosylate of the moiety, R, to be substituted on the nitrogen atom of the thiazine ring. This latter treatment preferably is conducted at temperatures below room temperature, for example, at 0°–15° C. The base used may be, for example, sodium, potassium or lithium hydrides, their hydroxides, or lower alkyls or alkoxides. A suitable liquid reaction medium for use with the metal hydride, alkyl or hydroxide thereof is tetrahydrofuran/hexamethylphosphoramide mixture. Where an alkoxide is used, it preferably is tertiary-butoxide and the solvent is tertiary butyl alcohol. In many cases, at least, it will not be necessary to isolate the intermediate product — the crude reaction mixture containing it may be treated with the R-sulfate, -iodide, -bromide, -chloride or -tosylate.

As has been indicated, most of the reactions should be conducted in a nitrogen atmosphere, and the techniques for recovery and purification of the intermediate and final products from the crude reaction mixtures are conventional and are illustrated in the examples indicated hereinafter.

Method D is carried out by heating a mixture of the thiazine and the olefinic compond in a suitable solvent at a moderately elevated temperature, for example, 60°–100° C. Suitable slvents include halogenated alkanes. Conduct of the reaction in 1,2-dichloroethane at its boiling point (refluxing at 83°–84° C) often is convenient.

In Method E, the thiazine compound (R = H), optionally in solution in a suitable solvent, optionally in the presence of a hydrogen halide acceptor, is treated with an equimolar quantity of a halogen or of a positive halogenating agent. Suitable positive halogenating agents are any of the conventional halogenating agents in which the halogen has a positive character, such as N-chloro- and N-bromosuccinimide. Water is ordinarily suitable and convenient as the solvent when chlorine or bromine is used as the halogenating agent. When a positive halogenating agent is used, the lower haloalkanes are suitable solvents. The reaction ordinarily can be effected under mild conditions, e.g., 0° C to about 45° C. To avoid di-halogenation, it is usually desirable to employ a temperature of the range of 5°–10° C and add the halogen slowly with vigorous stirring to avoid local excess of the halogen.

In Method F, the suitable alkylating agents include, for example, alkyl halides, sulfates, and tosylates. Suitable solvents include dimethylformamide, dimethyl sulfoxide, acetone, acetonitrile, nitrobenzene and sulfolane. The reaction is effected at a temperature of from about 20° to about 125°. The product can be isolated by precipitation with an inert solvent, or by concentration under reduced pressure. The nitromethylpotassium is readily prepared by treating nitromethane with t-butoxide in t-butanol. The reaction of the intermediate with nitromethylpotassium suitably is conducted in a solvent such as t-butanol, and at about room temperature. The product is isolated by dilution of the reaction mixture with water and extraction with a suitable solvent such as methylene chloride.

In Method G the suitable alkylating agents are those described for Method F, and the reaction suitably is conducted at a temperature of from about 50°–150°. If a slvent is used, lower haloalkanes are suitable.

In Method H, the suitable aldehydes are the haloaldehydes such as chloral, bromal, dichloroacetaldehyde and the like. The reaction proceeds at room temperature although warming may be desirable to insure completion of the reaction. Recovery and purification in this case, and in the case of Method G, are accomplished by conventional techniques.

In Method I, the thiazine reactant preferably is mixed with a small amount of a lower alkanol and the reactions are conducted at about room temperature. In some cases it may be necessary to heat the mixture to a moderately elevated temprature — e.g., about 50° C, to effect the reaction at a reasonable rate.

In Method J, the treatment is carried as described for Method I. Preparation of the precursor alcohol is described in Example 33.

In some cases, the product is non-basic in character so that it will not form a salt with the by-product hydrogen halide even when no acid acceptor is present. In such cases, the desired product can be recovered by extracting the reaction mixture with a suitable non-water soluble solvent, then evaporating the solvent. Suitable solvents are the halogenated alkanes such as methylene chloride. Where the product forms the salt, the product can be recovered by treating the reaction mixture with a base such as sodium bicarbonate to spring the product, then recovering it by solvent extraction of the aqueous mixture with a halogenated alkane.

Compounds of this invention may also be prepared by other methods, as illustrated in particular cases in the examples following.

All of these methods are illustrated in the following examples. In all cases, the identity of the product and the identity of any intermediate used was confirmed by appropriate analyses.

EXAMPLE 1

- Tetrahydro-2-(nitromethylene)-2H-1,3-thiazine (1A)

Method A 86.9 g of 3-amino-1-propanethiol was added to a suspension of 132 g of nitroketene dimethyl mercaptole in two liters of ethanol, and the mixture was stirred at 25° for 18 hours under nitrogen. The resulting solution was decanted from a small amount of tarry material and concentrated under reduced pressure to leave a viscous residue which was digested in 2 liters of water with one hour of vigorous stirring. The aqueous phase was separated from solid material, clarified by filtration and extracted with methylene chloride. The organic extract was dried (sodium sulfate) and concentrated under reduced pressure to give a yellow solid. The solid was washed with ether to give 1A as a yellow solid, m.p. 71°–74°.

EXAMPLE 2

Tetrahydro-2-(nitromethylene)-2H-1,3-thiazine (1B)

Method B

Ethyl nitro(tetrahydro-2H-1,3-thiazin-2-ylidene)-acetate (2A)

To a mixture of 235 g of 5,6-dihydro-2-(methylthio)-4H-1,3-thiazine and 2 g of zinc chloride at approximately 115° in a nitrogen atmosphere, 263 g of ethyl nitroacetate was added dropwise over a 1.5 hour period. The mixture was held at 110°–120°. When evolution of methyl mercaptan ceased after 45 minutes further stirring of the heated mixture, 1 g of zinc chloride was added and the mixture was stirred at about 115° for 1.25 hours. An additional 1 g of zinc chloride then was added and stirring of the mixture at about 115° was continued for 1.5 hours. The mixture then was poured into a cooled solution of 2/1 ether/isopropyl alcohol mixture. The crystallized product was collected, washed with ether and dried under reduced pressure to leave a tan solid, m.p. 100°–102°, which on recrystallization from methanol gave 2A as a pale yellow solid, m.p. 105°–106°.

2.3 g of 2A was added to 10 ml of 20% aqueous sodium hydroxide and the mixture was stirred at room temperature for 12 hours. The resulting solution was then treated dropwise with 3.5 g of acetic acid. The addition was accompanied by vigorous gas evolution. The resulting mixture was extracted with methylene chloride and the extract was dried (magnesium sulfate) and concentrated under reduced pressure to give 1B as a pale yellow solid, m.p. 76°–78°.

EXAMPLE 3

Tetrahydro-3-methyl-2-(nitromethylene) (3) -2H-1,3-thiazine

Method C

A solution of 4.8 g of 1B in 30 ml of tetrahydrofuran was added dropwise to a suspension of oil-free sodium hydride (from 1.35 g of a 57% mineral oil dispersion) in 30 ml of tetrahydrofuran and 10 ml of hexamethylphosphoramide, with stirring under nitrogen, the mixture being held at 23°–25° throughout the addition. Gas evolved. After 30 minutes, the reaction mixture was cooled to 5°–10° and a solution of dimethyl sulfate in 25 ml of tetrahydrofuran was added dropwise thereto. The mixture was stirred at 25°–35° for 1 hour, then poured into water and extracted with methylene chloride. The extract was dried (sodium sulfate) and concentrated under reduced pressure to leave a liquid. This was triturated with ether to give a gummy solid, m.p. 140°–145°. Recrystallization from ethyl acetate gave 3, as a pale yellow solid, m.p. 157°–158.5°.

EXAMPLE 4

2-(bromonitromethylene)-tetrahydro-2H-1,3-thiazine (4)

Method E

A solution of 3.2 g of bromine in 10 ml of methylene chloride was added dropwise to a solution of 3.2 g of 1B in 50 ml of water, the temperature being held at 5°–10°. The mixture was then stirred for 45 minutes when 200 ml of methylene chloride was added to dissolve the solid material. The organic phase was separated, washed with water, dried (sodium sulfate) and concentrated under reduced pressure to give a yellow solid. This was washed with ether to give 4, as a yellow solid, m.p. 122° (with decomposition).

EXAMPLES 5 and 6

3-benzyl-tetrahydro-2-(nitromethylene)-2H-1,3-thiazine (5)
tetrahydro-2-(1-nitro-2-phenylethylidene)-2H-1,3-thiazine (6)

Method C

A solution of 8.0 g of 1B in 40 ml of tetrahydrofuran was added dropwise to a suspension of oil-free sodium hydride (from 2.3 g of a 50% oil dispersion) in a mixture of 20 ml of tetrahydrofuran and 10 ml of hexamethylphosphoramide, stirred under nitrogen and maintained at 15°–30°. After 45 minutes of stirring, a solution of 9.4 g of benzyl bromide in 10 ml of tetrahydrofuran was added dropwise, the temperature of the mixture being held at 6°–8°. The mixture was stirred for 2 hours at 25° and 2 hours at reflux temperature, then allowed to stand at room temperature overnight. Then 200 ml of ice water was added and the resulting mixture was extracted with methylene chloride, and the extract was washed with saturated salt solution. The extract was dried (sodium sulfate) and concentrated under reduced pressure to give 13.4 g of an amber oil. Dry-column chromatography, first on silica gel with a 1:1:2 mixture of tetrahydrofuran, ethyl acetate and hexane, and then on silica gel with a 3:5:12 mixture of methylene chloride hexane and ethyl acetate, gave two fractions, one an organge solid, m.p.: 109°–113° and one a yellow solid, m.p.: 148°–154°. Recrystallization of the first fraction from ethyl acetate provided 5, as a yellow solid, m.p.: 141.5°–143.5°. Recrystallization of the second fraction from ethyl acetate gave 6, as a yellow solid, m.p.: 156°–157.5°.

EXAMPLE 7

Tetrahydro-2-(nitromethylene)-3-propyl-2H-1,3-thiazine (7)

Method F

A solution of 19.6 g of 5,6-dihydro-2-(methylthio)-4H-1,3-thiazine and 30.0 g of propyl iodide in 50 ml of dimethyl formamide was allowed to stand for 15 hours and then heated in a steam bath for 45 minutes. The solution was poured into 750 ml of ether and the oil which settled out was separated and stripped under high vacuum at 55°–60° to leave an amber oil with appropriate spectral features for the propiodide salt. A solution of 13.0 g of this oil in 15 ml of methylene chloride was added dropwise to a suspension of the potassium salt of nitromethane in tertiary-butyl alcohol (prepared by treating 5.0 grams of nitromethane with 4.8 g of potassium tert-butoxide in 30 ml of tert-butyl alcohol at 23°–25°). The reaction mixture was stirred at room temperature for 18 hours under nitrogen, diluted with 600 ml of methylene chloride, and washed with water and with saturated salt solution. The organic phase was dried (sodium sulfate) and concentrated under reduced pressure to leave a slightly gummy yellow-orange solid. This material was boiled in 150 ml of ether containing 20 ml of ethyl acetate and the resulting solid residue was chromatographed on silica gel using the dry-column technique. Development with 49:1 ethyl acetate/methanol mixture gave two principal portions. The more polar, a yellow solid, m.p. 130°–144°, was washed with ether to give a solid identified as 7. The less polar portion (a yellow solid, m.p. 144°–170°) was dissolved in chloroform, the solution was treated with charcoal, filtered and concentrated to dryness. The residue was washed with ether to give more 7 as a light solid, m.p. 159°–161°.

EXAMPLE 8

3-ethyl-tetrahydro-(nitromethylene)-2H-1,3-thiazine (8)

Method F 14.7 g of 5,6-dihydro-2-methylthio-4H-1,3-thiazine was added dropwise to a solution of 62.4 g of ethyl iodide in 100 ml of dimethylformamide at 75°. The mixture was stirred for 2 hours under nitrogen at about 75° and then concentrated under high vacuum to leave a viscous, dark-orange liquid identified by spectral analyses as 3-ethyl-5,6-dihydro-2-methylthio-4-H-1,3-thiazinium iodide (8A). A solution of 27.1 g of 8A in 40 ml of methylene chloride was added dropwise at 25° to a suspension of nitromethylpotassium (prepared from 11.2 g of potassium tert-butoxide and 13 g of nitromethane in tert-butanol). The reaction mixture was stirred under nitrogen for 18 hr. at 25°, then diluted with 600 ml of methylene chloride. The organic phase was washed with water and with saturated salt solution, dried (sodium sulfate) and concentrated under reduced pressure to leave a gummy, yellow solid, m.p.: 75°–80°. This solid was heated for 1 hour in ether, then the solid residue was separated, being orange-yellow in color, m.p.: 120°–138°. Chromatography on silica gel using a 1:1:2 mixture of tetrahydrofuran/ethyl acetate/hexane as eluent followed by trituration of the product with ether gave 8 as a light yellow solid, m.p.: 156°–161°.

EXAMPLE 9

5-nitro-5-(tetrahydro-2H-1,3-thiazin-2-ylidene)-2-pentanone (9)

Method D

Under a nitrogen atmosphere, 1.9 g of methyl vinyl ketone was added dropwise to a solution of 4.0 g of 1B in 10 ml of methylene chloride at 25°. After stirring for 72 hours, the mixture was concentrated under reduced pressure to give a pale-yellow solid which was washed with ether and dried to give 9, m.p.: 118°–120°.

EXAMPLE 10

2-(chloronitromethylene)-tetrahydro-2H-1,3-thiazine (10)

Method E

A mixtue 16.0 of 1B and 13.4 g of N-chlorosuccinimide in 250 ml of carbon tetrachloride was stirred at room temperature for 21 hours. The resulting mixture was filtered and the solids were extracted with methylene chloride. The organic liquid phase was washed with water, dried (magnesium sulfate) and concentrated under reduced pressure to leave an orange-yellow solid, chromatography on silica gel with 1:1 methylene chloride/ethyl acetate mixture was eluent gave 10, as a yellow solid, m.p.: 140°–141°.

EXAMPLE 11

Tetrahydro-2-(2-methoxycarbonyl)ethyl)nitromethylene)-2H,1,3-thiazine (11)

Method D

A solution of 4.0 g of 1B and 2.5 g of methyl acrylate in 50 ml of 1,2-dichloroethane was refluxed under nitrogen for 34 hours. The reaction mixture was concentrated under reduced pressure and chromatographed through florisil with a 99:1 methylene chloride/methanol mixture as eluent to give a yellow solid. Recrystalization of the solid from ether/ethyl acetate/pentane mixture gave 10, as a pale yellow solid, m.p.: 82–83°.

EXAMPLE 12 -

((2-cyanoethyl)nitromethylene)tetrahydro-2H-1,3-thiazine (12)

Method D

A solution of 5.0 g of 1B and 1.8 g of acrylonitrile in 50 ml of 1,2-dichloroethane was refluxed under nitrogen for 24 hours. Then 5.4 g of additional acrylonitrile was added and the mixture was refluxed for 18 hours. Then 5.4 g of acrylonitrile was added and a further 5.4 grams was added 4 hours later. The mixture was refluxed during this period and for 18 hours thereafter. The mixture was concentrated under reduced pressure to leave a dark, gummy solid. The solid was chromatographed on florisil using a 88:1 methylene chloride/methanol mixture as eluent to give two fractions: (a) yellow solid, m.p.: 135°–145°, and (b) yellow solid, m.p.: 142°–151°. Fraction (a) was recrystallized from ethyl acetate to give 12, as a yellow solid, m.p.: 144°–145°. Fraction (b) was washed with ether to give more 12, as a yellow solid, m.p.: 142°–144°.

EXAMPLE 13 -

Tetrahydro-2-(1-nitro-3-butenylidene)-2H-1,3-thiazine (13)

Method G

A mixture of 16.0 of 1B and 100 ml allyl bromide was refluxed under nitrogen for 5 hours. After cooling, the mixture was diluted with methylene chloride and washed with saturated sodium bicarbonate solution and with water. The organic phase was dried (sodium sulfate) and concentrated under reduced pressure to give a dark oil which was crhomatograhed on florisil using 99:1 methylene chloride/methanol mixture as eluent to give a red oil. Crystallization from ether gave 13 as a light orange solid, m.p.: 55°–56°.

EXAMPLE 14 -

1,1,1-trichloro-3-nitro-3-(tetrahydro-2H-1,3-thiazin-2-ylidene)-2-propanol (14)

Method H 4.0 g of chloral was added dropwise to a solution of 4.0 g of 1B in 50 ml of methylene chloride. The solution was stirred at room temperature uner nitrogen for 18 hours. Solid that formed was collected and washed with methylene chloride to leave 14 as a pale yellow powder, m.p.: 131°–131.5°.

EXAMPLE 15 -

N,N-dimethyl-2-nitro-2-(tetrahydro-2H-1,3-thiazine-2-ylidine)ethanamine (15)

Method I 5 g of 25% aqueous dimethylamine was added to a slurry of 4 grams of 1B in 12 ml of ethanol. Then, with external cooling, 2.3 g of 37% aqueous formaldehyde was added at 24°–27°. The mixture then was stirred for 2 hours at 25°, then was diluted with water and extracted with methylene chloride. The extract was dried and concentrated under reduced pressure to leave a yellow solid. This solid was washed with ether and air dried to give 15 as a yellow solid, m.p.: 100.5°–101°.

EXAMPLES 16 – 22

In a manner similar to that described in Example 15:

a. N,N-diethyl-2-nitro-2-(tetrahydro-2H-1,3-thiazin-2-ylidene)ethanamine (16) was prepared as a yellow solid, m.p.: 68°–69°;
b. tetrahydro-2-(1-nitro-2-(1-pyrrolidino)ethylidene)-2H-1,3-thiazine (17) was prepared as a pale yellow solid, m.p.: 102°–103°;
c. tetrahydro-2-(1-nitro-2-(1-piperidino)ethylidene)-2H-1,3-thiazine (18) was prepared as a pale yellow solid, m.p.:j 115°–116°;
d. 4-(2-nitro-2-(tetrahydro-2H-1,3-thiazin-2-ylidene)ethyl)morpholine (19) was prepared as a pale yellow solid, m.p.: 131°–132.5°;
e. N-(2-nitro-2-(tetrahydro-2H-1,3-thiazin-2-ylidene)-N-(2-propenyl)-2-propen-1-amine (20) was prepared as a yellow solid, m.p.: 59°–61.5°;
f. N-(2-nitro-2-(tetrahydro-2H-1,3-thiazin-2-ylidene)ethyl)-N-phenylmethylbenzenemethanamine (21) was prepared as a pale yellow solid, m.p.: 108°–110.5°;
g. N-methyl-N-(2-nitro-2-(tetrahydro-2H-1,3-thiazin-2-ylidene)ethyl)benzenamine (22)

EXAMPLE 23 -

3-ethyltetrahydro-2-(nitromethylene)-2H-1,3-thiazine (23)

35 ml of tert-butyl lithium was added dropwise at −10° to a solution of 8.0 g of 1B in 100 ml of tetrahydrofuran. The mixture was stirred for 5 minutes at −10°, then 32 g of ethyl iodide was added at −5° to −15°, and the mixture was stirred at −15° for 15 minutes. The mixture then was warmed and stirred at room temperature for 24 hours, then stirred at reflux temperature for 24 hours, then cooled to 25°, 10 ml of hexamethylphosphoramide added and the mixture stirred at reflux temperature for 7 hours, then at room temperature overnight. The resulting mixture was diluted with methylene chloride, the resulting solution washed with saturated sodium chloride solution, dried and the solvent evaporated under reduced pressure to give an amber oil. This oil was chromatographed on silica gel, by dry column technique, using a 40/8/2 mixture of hexane, ethyl acetate and tetrahydrofuran, to give 23 as an amber oil, boiling point not determined.

EXAMPLE 24 - tetrahydro-2-(1-nitro-3-butynylidene)-2H-1,3-thiazine (24)

A stirred mixture of 6 g of 1B, 30 ml of tertiary butyl alcohol and 30 ml of propargyl bromide was heated to reflux for 3 hours, then was allowed to stir at room temperature over a week-end, after which it was heated to reflux and stirred for 5.5 hours. The mixture then was cooled, diluted with methylene chloride, washed with saturated sodium bicarbonate solution and water. The organic phase then was dried, and the solvent evaporated under reduced pressure. The residue was passed through florisil, using methylene chloride as eluent, to give a gummy liquid, which when dissolved in isopropyl alcohol gave a brown solid, which on recrystallization from isopropyl alcohol gave 24, as a brown solid, m.p.: 132°–135°.

EXAMPLE 25 -

2-(2-(ethylthio)-1-nitroethylidene)-tetrahydro-2H-1,3-thiazine (25)

At 5°–10°, a solution of 1.75 g of ethanethiol in 5 ml of ethanol was added all at once to a mixture of 4.0 g of 1B in 50 ml of 50% ethanol. Then at 5°, 2.3 g of 37% aqueous formaldehyde was added dropwise and the mixture stirred for 2 hours at 5° and at room temperature overnight. It then was poured into methylene chloride, the methylene chloride solution washed with saturated sodium chloride solution and the solvent evaporated under reduced pressure. The resulting oil was passed through florisil, using a 99:1 methylene chloride/methanol mixture to give a pale yellow solid, which was washed with ether to give 25, as a pale yellow solid, m.p.: 69.5°–71°.

EXAMPLE 26 -

2-(2-(ethylsulfinyl)-1-nitroethylidene)tetrahydro-2H-1,3-thiazine (26)

A mixture of 2.34 g of 25 and 10 ml of acetone was added all at once to a solution of 2.25 g of sodium periodate in 15 ml of water. The resulting exothermic reaction was controlled between 25° and 35° by cooling. The mixture then as stirred at room temperature for 90 minutes, then was poured into a mixture of water and methylene chloride. The separated organic phase was washed with saturated sodium thiosulfate solution, and saturated sodium chloride. It then was dried (MgSO$_4$) and the solvent evaporated under reduced pressure to give an oil, which was triturated with ether to give a yellow solid. This was chromatographed by a preparative thin layer chromatographic technique, on silica gel and using a mixture of methanol (2%) in methylene chloride as eluent, to give 26, as a yellow solid, m.p.: 102°–104°.

EXAMPLE 27 -

Sodium salt of 1B (27)

4.0 g of 1B was added to a solution of 1.0 g of sodium hydroxide in 25 ml of water at room temperature. The resulting mixture was filered through Celite to give 27, as an approximatey one molar solution in water.

EXAMPLE 28 -

HCl salt of 18 (28)

0.4 g of gaseous hydrogen chloride was bubbled into a mixture of 2.57 g of 18 in 50 ml of methylene chloride, at room temperature. The solent was evaporated under reduced pressure. The residue was washed with ether and dried to give 28 as a tan solid, m.p.: 119°–121°.

EXAMPLES 29 – 31

By the procedure of Example 28 were prepared compounds 29, 30 and 31, the HCl salts of:
a. 19, as a white solid, m.p.: 132.5°–133°;
b. 15, as a tan solid, m.p.: 112.5°–113°;
c. 1B, as a beige solid, m.p.: 123°–125°.

EXAMPLE 32 - methyl iodide salt of 18 (32)

A solution of 4.26 g of methyl iodide in 10 ml of ethanol was slowly added to a cold (5°–10°) mixture of 5.14 g of 18 in 25 ml of ethanol, then 10 ml of methylene chloride was added. The mixture was stirred at room temperature for 2.5 hours. Then 50 ml of ether was added, the solid was collected and washed with additional ether to give 32, as a yellow solid, m.p.: 120°–121.5°.

EXAMPLE 33 -

2-nitro-2-(tetrahydro-2H-1,3-thiazin-2-ylidene)ethanol (33)

36.8 ml of 37% formaldehyde in water was added dropwise over a 30-minute period to a slurry of 32 g of 1B in 120 ml of ethanol and 2 g of triethylamine (as catalyst), at 5°–10°. 30 ml of ethanol and 20 ml of water were added to facilitate stirring and the mixture was stirred overnight. The solid which formed was separated by filtration and was washed with ethanol and ether, then was dried in a vacuum oven to give 33, as a light yellow solid, m.p.: 132°–133° (with decomposition).

EXAMPLE 34 - tetrahydro-2-(nitro(phenylthio)methylene)-2H-1,3-thiazine (34)

7.2 g of benzenesulfenyl chloride in 25 ml of methylene chloride was added dropwise to 8.0 g of 1B and 5.1 g of triethylamine in 100 ml of methylene chloride at 0°–10° under an argon atmosphere. The cold mixture was stirred for 30 minutes, then at room temperature for 1 hour. 300 ml of methylene chloride was added, the mixture washed with after and with saturated sodium chloride solution. The separated organic phase was dried and the solvent removed under reduced pressure. The residue was washed with ethyl acetate to give 34, as a brown solid, m.p.: 144.5°–147°.

EXAMPLE 35 - tetrahydro-2-((4-methoxyphenylthio)-nitromethylene)-2H-1,3-thiazine (35)

was prepared as a yellow solid, m.p.: 160°–162°, from 1B and (4-methoxyphenyl)sulfenyl bromide according to the procedure of Example 34.

EXAMPLE 36 -

2,2'-(1,3-dinitro-1,3-propanediylidene)bis-(tetrahydro)-2H-1,3-thiazine (36)

8 g of 1B, 6.6 ml of 37% formalin, 50 ml of methanol and 2 drops of concentrated sulfuric acid were mixed and the mixture heated in a steam bath for 30 minutes. The mixture was cooled with ice and filtered to give 36, as a yellow solid, m.p.: 195°, with decomposition.

EXAMPLE 37 -

3-(tetrahydro-2-(nitromethylene)-2H-1,3-thiazin-2-yl)-2-propenoic acid, methyl ester (37)

4.2 g of methyl propiolate was added to a solution of 8 g of 1B in 50 ml of methanol at room temperture. After two hours, 5 drops of 1,1,3,3-tetramethylguanidine was added. The reaction mixture temperature rose to 36° after 1 hour. The solvent was evaporated under reduced pressure, and the residue was chromatographed using ethyl acetate as eluent to give 37, as a yellow solid, m.p.: 128°–140°.

EXAMPLE 38 -

3-(tetrahydro-2-(nitromethylene)-2H-1,3-thiazin-2-yl)-2-propenoic acid, ethyl ester (38)

By the procedure described in Example 37, 38 was prepared as a yellow solid, m.p.: 112°–120°.

EXAMPLE 39

By the general procedure described in Example 15, 3,4-dichloro-N-(2-nitro-2-(tetrahydro-2H-1,3-thiazin-2-ylidene)ethybenzene amine (39) was prepared, as a bright yellow solid, m.p.: 132°–133°, from 1B, formaldehyde and 3,4-dichloroaniline.

EXAMPLE 40 -

2,4-dichloro-N-(2-nitro-2-(tetrahydro-2H-1,3-thiazin-2-ylidene)ethybenzene amine (40)

3.9 g of 2,4-dichloroaniline was added, in several parts, to a solution of 3.7 g of 33 in 25 ml of ethanol at 10°. The mixture was stirred for 2 hours, being allowed to warm to room temperature. It then was stirred and heated gently, to 50°, for 1.5 hours. It then was allowed to stir overnight at room temperature. The solid product was separated by filtration. It was washed with isopropyl alcohol, then with ether and airdried. The residue was stirred in methylene chloride for 15 minutes. The mixture was filtered, the filtrate was washed with 5% sodium hydroxide solution, then was dried and the solvent was evaporated to give 40, as a light yellow solid, m.p.: 122°–124°.

The compounds of this invention exhibit useful insecticidal activity, being of particular interest for control of the larvae "caterpillar" or "worm" forms of insects of the genus Heliothis, such as *H. zea* (corn earworm), cotton bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littoralis* (Egyptian cotton leafworm). Some are also of interest for controlling whiteflies and houseflies. In tests that have been conducted they have exhibited low, or no, toxicity to other insects such as the 2-spotted spider mite and mosquito larva. Some act very rapidly, providing "quick knock-down" of insects, in some cases even though the compound is not very toxic to the insects.

Activity of compounds of this invention with respect to insects was determined by using standardized test methods to establish the $LC_{50}$ dosage (in milligrams of test compound per 100 milliliters of solvent or liquid carrier required in the solution of suspension of test compound used) that was requied to kill 50% of the test insects. The test insects were housefly, corn earworm, pea aphid and 2-spotted spider mite, and in some cases the black cutworm. Activity with respect to mosquito larvae was determined by placing the larvae in water containing the test compound.

All of compounds 1A through 40 were found to be inactive or but slightly active with respect to the mites and mosquito larvae. With respect to the corn earworm all of compounds 1A - 40 were found to be active. With respect to the housefly, compounds 1A - 4, 7 - 10, 12 - 21, 24, 27 - 35 and 37 were found to be active. With respect to the pea aphid compounds 1A - 5, 7 - 10, 12 - 25, 27 - 34 and 36 - 38 were found to be active. Compounds 1 and 4 also were tested and found to be highly active with respect to the black cutworm.

In the course of these tests it was noted that compounds 4, 7 - 9, 13 - 15, 18, 27, 32 and 33 acted very quickly on houseflies, compounds 1A, 8, 12 - 14, 16, 21 - 22, 24, 27 and 29 - 33 acted very quickly on pea aphids and compounds 1A, 4, 7 - 9, 11 - 16, 18 - 21, 24, 27, 29, 31, 35 and 36 acted very quickly upon corn earworms.

The invention includes within its scope insecticidal compositions comprising an adjuvant -- that is, a carrier, optionaly a surface-active agent -- and, as active ingredient, at least one insecticide of this invention. Likewise the invention includes also a method of combatting insect pests at a locus which comprises applying to the locus an effective amount of at least one insecticide of the invention.

The term "carrier" as used herein means a material, which may be inorganic or organic and of synthetic or natural origin with which the active compound is mixed or formulated to faciliate its application to the plant, seed, soil and other object to be treated, or its storage, transport or handling. The carier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compunds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated cater oil, and sodium alkaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3-10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, graules will contain ½-25%w toxicant and 0- 10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosages of toxicants of this invention at the locus to be protected -- i.e. the dosage to which the insect contacts -- is of the order of 0.001% to 0.5% based on the total weight of the formulation, though under some circumstances the effective concentration will be as little as 0.0001% or as much as 2%, on the same basis.

I claim as my invention

1. A resonance hybrid in which the two significant forms which contribute thereto are represented by the formula

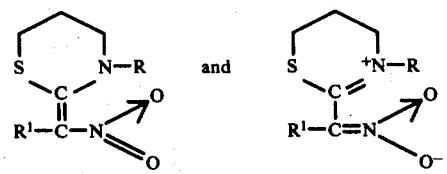

and including when R is hydrogen, the tautomeric form represented by the formula

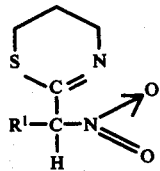

wherein R is hydrogen, or contains up to eight carbon atoms and is alkyl, alkenyl, alkoxyalkyl, cycloalkylalkyl, cyanoalkyl, haloalkenyl, phenalkyl or alkoxycarbonylvinyl.

$R^1$ is hydrogen or contains up to eight carbon atoms and is alkyl, alkenyl, alkynyl, haloalkyl, haloalkenyl, halo(hydroxy)alkyl, alkoxyalkyl, cyanoalkyl, hydroxyalkyl, alkoxycarbonylalkyl, alkylcarbonylalkyl, alkylthioalkyl, alkylsulfinylalkyl, phenalkyl or phenylthio optionally substituted on the ring by one or more of halogen, nitro, cyano, alkyl, phenyl, alkoxy or phenoxy; halogen; aminomethyl, —CH$_2$-NR$^2$R$^3$, R$^2$ is alkyl, hydroxyalkyl, alkoxyalkyl, cycloalkyl, alkenyl, phenyl or phenalkyl, and $R^3$ is hydrogen or one of the moieties represented by $R^2$;

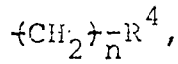

wherein n is zero, one or two, and $R^4$ is a heteromonocyclic moiety of from five to six carbon atoms in the ring, containing in the ring carbon atoms and one to two of oxygen (—O—), sulfur (—S—) and nitrogen (=N- or -NH-) bonded to carbon in the ring; or is

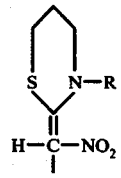

and salts of such compounds in which R is hydrogen.

2. A resonance hybrid according to claim 1 wherein R is hydrogen.

3. A resonance hybrid according to claim 2 wherein $R^1$ is hydrogen.

4. A resonance hybrid according to claim 2 wherein $R^1$ is bromine.

5. A resonance hybrid according to claim 2 wherein $R^1$ is dimethylaminomethyl.

6. A resonance hybrid according to claim 2 wherein $R^1$ is 1-piperidinomethyl.

7. A resonance hybrid according to claim 2 wherein $R^1$ is 4-morpholinomethyl.

* * * * *

UNITED STATES PATENT AND TRADEMARK OFFICE
CERTIFICATE OF CORRECTION

PATENT NO. : 3,993,648

DATED : November 23, 1976

INVENTOR(S) : James. E. Powell

It is certified that error appears in the above-identified patent and that said Letters Patent are hereby corrected as shown below:

Claim 1:

At line 9, column 2, the period should be a semicolon.

At line 2, column 18, the period should be a semicolon.

Signed and Sealed this

Third Day of May 1977

[SEAL]

Attest:

RUTH C. MASON
Attesting Officer

C. MARSHALL DANN
Commissioner of Patents and Trademarks

UNITED STATES PATENT AND TRADEMARK OFFICE
CERTIFICATE OF CORRECTION

PATENT NO. : 3,993,648
DATED : November 23, 1976
INVENTOR(S) : James E. Powell

It is certified that error appears in the above-identified patent and that said Letters Patent are hereby corrected as shown below:

Column 2, line 9, change the period to a semicolon;

line 25, cancel "carbon";

line 27, change "and" to --or--;

lines 30-35, change the formula from

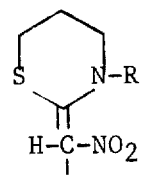

to

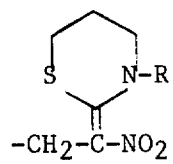

UNITED STATES PATENT OFFICE
CERTIFICATE OF CORRECTION

Patent No. 3,993,648      Dated November 23, 1976

Inventor(s) James L. Powell

It is certified that error appears in the above-identified patent and that said Letters Patent are hereby corrected as shown below:

Column 18, line 2, change the period to a semicolon;

line 19, cancel "carbon";

line 21, change "and" to --or--;

lines 25-30, change the formula from

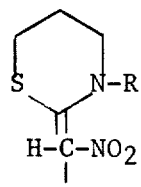

UNITED STATES PATENT OFFICE
CERTIFICATE OF CORRECTION

Patent No. 3,993,068  Dated November 23, 1976

Inventor(s) James C. Powell

It is certified that error appears in the above-identified patent and that said Letters Patent are hereby corrected as shown below:

to

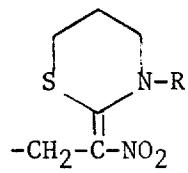

This certificate is to supersed Certificate which issued May 3, 1977.

Signed and Sealed this

Thirty-first Day of January 1978

[SEAL]

Attest:

RUTH C. MASON
Attesting Officer

LUTRELLE F. PARKER
Acting Commissioner of Patents and Trademarks